United States Patent
Demmer et al.

(10) Patent No.: US 6,235,892 B1
(45) Date of Patent: May 22, 2001

(54) PROCESS FOR THE PURIFICATION OF NUCLEIC ACIDS

(75) Inventors: Wolfgang Demmer; Dietmar Nussbaumer, both of Göttingen (DE)

(73) Assignee: Sartorius AG (DE)

( * ) Notice: Subject to any disclaimer, the term of this patent is extended or adjusted under 35 U.S.C. 154(b) by 0 days.

(21) Appl. No.: 09/468,706

(22) Filed: Dec. 21, 1999

(30) Foreign Application Priority Data

Jan. 4, 1999 (DE) .............................................. 199 00 681

(51) Int. Cl.⁷ ..................................................... C07H 21/00
(52) U.S. Cl. ................... 536/25.4; 536/25.41; 536/25.42
(58) Field of Search ................ 536/25.4, 25.41, 536/25.42

(56) References Cited

U.S. PATENT DOCUMENTS

| | | | |
|---|---|---|---|
| 4,791,063 | * 12/1988 | Hou et al. | 435/243 |
| 4,935,342 | * 6/1990 | Seligson et al. | 435/6 |
| 4,997,432 | * 3/1991 | Reardon et al. | 536/25.4 |
| 5,136,032 | * 8/1992 | Nagamatsu et al. | 536/187 |
| 5,438,128 | * 8/1995 | Nieuwkerk et al. | 536/25.4 |
| 5,547,575 | * 8/1996 | Demmer et al. | 210/490 |
| 5,618,418 | 4/1997 | Demmer et al. | 210/232 |
| 5,637,687 | * 6/1997 | Wiggins et al. | 536/25.4 |
| 6,001,974 | * 12/1999 | Demmer et al. | 530/364 |

FOREIGN PATENT DOCUMENTS

| | | |
|---|---|---|
| 0 853 123 A1 | 12/1995 | (EP) . |
| 0 527 992 B1 | 2/1998 | (EP) . |
| 0 538 315 B1 | 7/1998 | (EP) . |
| 9311218 | * 6/1993 | (WO) . |
| 9749834 | * 12/1997 | (WO) . |
| 9841302 | * 9/1998 | (WO) . |
| 9960005 | * 11/1999 | (WO) . |

* cited by examiner

Primary Examiner—Gary Geist
Assistant Examiner—L. E. Crane
(74) Attorney, Agent, or Firm—Chernoff, Vilhauer, McClung & Stenzel, LLP

(57) ABSTRACT

There is disclosed a membrane process for the purification of nucleic acids in aqueous solutions whereby a lasting reduction of endotoxin content is achieved. The process is suitable for small or large volumes and can be carried out quickly and with simple apparatus.

3 Claims, No Drawings

PROCESS FOR THE PURIFICATION OF NUCLEIC ACIDS

Pursuant to 35 USC §119, the priority of DE 199 00 681.4 filed Jan. 4, 1999 is claimed.

BACKGROUND OF THE INVENTION

Because of the increasing use of nucleic acids in animal and human medicine, such as in gene therapy, there has been a growing need for making these materials available in greater purity. The term "nucleic acids" is to be understood as a collective term, encompassing deoxyribonucleic acids (DNA), ribonucleic acids (RNA), antisense RNA and nucleic acids with modified bases or structure. Endotoxins from gram-negative bacteria such as E. coli are often present in nucleic acids and when, during the course of recovery and isolation of such acids, particles of bacterial cell walls are not completely eliminated, there exists the possibility of the endotoxins finding their way to the final nucleic acid solutions being used in, say, a medical study. The introduction of endotoxins into patients must, of course, be avoided at all costs, since, where humans and experimental animals are concerned, endotoxins cause serious symptoms of illness, including fever and inflammation of blood vessels, activate blood-clotting and stimulate the production of antigens by the immune system.

EP 0 853 123 A1 discloses a process for the purification of nucleic acids in aqueous solutions, in which the solution containing nucleic acid and not cleared of endotoxins is flowed tangentially over ultrafiltration membranes with exclusion limits of 1 to 1000 kilodaltons. When this is carried out, because of its large size, a molecule of nucleic acid should not pass the membrane. At the same time, substances of lesser molecular weight, such as endotoxins, migrate through the membrane and/or are adsorbed on the membrane. The disadvantages of such an ultrafiltration technique are the considerable cost of the necessary apparatus, the large amount of time consumed (by virtue of the relatively low filtration speed common to the use of ultrafiltration membranes), the requirement for using large volumes of liquid feed solution (making the procedure unsuitable for laboratory scale work) and the tendency for dissolved proteins to prematurely blind the membranes.

These disadvantages are overcome by the present invention, which provides a process which can be carried out quickly and simply for the purification of aqueous solutions of nucleic acids, by which a lasting reduction of the endotoxin content is achieved, and which is suitable for both large- and small-scale treatments.

BRIEF SUMMARY OF THE INVENTION

The process of the present invention comprises filtering an endotoxin-containing aqueous nucleic acid feed solution through at least one layer of a microporous weakly basic anion exchange membrane, thereby binding both endotoxins and nucleic acid(s) onto the membrane. Particles greater in size than the pores of the anion exchange membrane are excluded from passage through the membrane and are restrained on the feed side of the membrane array. Subsequently, bound nucleic acid(s) are selectively eluted from the membrane by a buffered neutral salt solution having a higher ionic strength than the nucleic acid feed solution, leaving endotoxins bound to and/or adsorbed onto the membrane. The process results in the recovery of an essentially endotoxin-free nucleic acid solution. Optionally, the nucleic acid elution step may be preceded by a washing with a buffer of lesser ionic strength than that of the elution solution, in order that impurities such as proteins, which have collected in membrane's pores or are weakly bound to the membrane may be separated therefrom.

DETAILED DESCRIPTION OF PREFERRED EMBODIMENTS

In a preferred embodiment of the invention, the aqueous nucleic acid feed solution is adjusted to a pH in the range of 5 to 9.5 and has an ionic strength of $\leq 0.1M$, while the pH of the buffered neutral salt solution is adjusted to a value of 5 to 9.5 with an ionic strength of from about 0.5 to about 3M. In a particularly preferred embodiment, the pH of the feed solution is adjusted to about 8 and its ionic strength is about 0.01M, while the pH of the buffered neutral salt solution is about 5.5 with an ionic strength of between about 1 and 2 M, and most preferably 0.7 M when sodium chloride is the neutral salt.

For increasing the security of the filtration and the capacity for purification, more than one layer of the membrane may be employed, particularly in the form of a laminated pack as is described in U.S. Pat. No. 5,618,418 or a wound filter as taught in DE OS 197 11 083, the pertinent disclosures of which are incorporated herein by reference. The membranes can also be in the form of one or more pleated membrane cartridges, as they are usually used in sterile filtration.

Suitable weakly basic anionic exchange membranes include those containing primary, secondary or tertiary amine groups, which are affixed to the membrane either singly or in combination with one another. Such membranes are based on immobilizing weakly basic groups onto the surface of large pore size, modified membranes such as cellulosic membranes, with diethylamine for example being the weakly basic anion exchanger. Such a membrane is commercially available from Sartorius AG of Gottingen, Germany and sold as Sartobind®D.

A preferred subset of such anion exchange membranes are those which possess predominately or exclusively tertiary aliphatic amines as the ion exchange groups, wherein at least one of the alkyl groupings contain 2 to 5 carbon atoms with those containing 3 or more carbon atoms being branched or straight chain. A particularly preferred ion exchange group is a tertiary amine, having two ethyl groups. Such membranes preferably have a pore size range of from 0.01 to 30 $\mu$m, even more preferably of from 0.1 to 8 $\mu$m. The membranes in accord with the invention should not be confused with those anion exchange membranes used in electrodialysis, even though the pore size ranges may be the same as those preferred in the present invention. See EP 0 538 315 B1 and EP 0 527 992 B1. Other membranes suitable for use in the present invention are polyamides, polysulfones and polyvinylidene fluoride.

In the filtration of an aqueous nucleic acid- and endotoxin-containing feed solution through a weakly basic anion exchange membrane, both nucleic acids and endotoxins are bound to the membrane, probably by an ionic mechanism. The binding occurs not only on the outer surface of the membrane, but also on the inner surfaces of the membrane pores.

In a rather surprising aspect of the present invention, the inventors have discovered, that upon subsequent contact with a neutral salt solution of relatively higher ionic strength than the feed solution, the nucleic acid component is selectively eluted, meaning that it is reversibly bound, while at least a majority of the endotoxin component remains irreversibly bound to and/or adsorbed onto the membrane. This effect does not occur with the use of strongly basic anion exchange membranes, such as, for example, Sartobind™ Q type membranes (Sartorius AG); specifically, while the strongly basic anion exchange membranes do bind both the nucleic acid and endotoxin components, upon subsequent contact with a neutral salt solution of a higher ionic strength both components are eluted, thus permitting endotoxins to pass through the membrane along with nucleic acid(s), an undesirable result. Porous membranes having no ion exchange groups are likewise unsuitable for purification of nucleic acids. Thus, for example, a polypropylene membrane adsorbs both endotoxins and nucleic acids irreversibly, so that selective elution of one of the two substances is not possible.

The anion exchange membranes used in the present invention exhibit a high flux, so that filtration time is held to a minimum. The use of the anion exchange membranes enables the filtration of both small and large volumes, the latter containing nucleic acids in extremely dilute concentrations. This is due to the fact that the nucleic acid molecules are ionically bound by the filtration through the membrane and can subsequently be eluted from the membrane with relatively small liquid volumes. This leads to a concentration effect of several orders of magnitude. If essentially micro-quantities of nucleic acids are only available (as in the case of lab work), it has proven useful to employ a small centrifugation tube as a separation means to be used in conjunction with weakly basic anion exchange membranes. Such an apparatus is commercially available as Centribind® D (Sartorius AG).

The invention will be more fully understood by study of the following examples. In the examples, endotoxin from the firm Pyroquant, Charge 11717 was used and the quantitative determination of endotoxin concentration was accomplished with the Limulus Amoebo-Lysat Test (LAL Test) of Pyrogent, Ch. 2196, sensitivity 6 pg/mL. Weakly basic anion exchange membranes (Sartobind® D) were used, as well as strongly basic anion exchange membranes (Sartobind® Q). Polypropylene (PP) membranes having a nominal pore diameter of 0.2 $\mu$m were from Akzo Nobel, class 2EPPHF, type 0884.

Example 1

Three-membrane arrays of 25 mm diameter membranes of the weakly basic anion exchange membrane, the strongly basic anion exchange membrane and the polypropylene membrane were placed in stainless steel filter holders and first flushed through with 20 mL of water for rinsing and wetting the membranes. Subsequently, 5 mL of a feed solution of 100 $\mu$g DNA of the plasmid pSE 420 (order number E7772 from SIGMA, of Deisenhofen, Germany) and 3 $\mu$g/mL endotoxin in a buffer of the composition 10 mM tris-HCl, pH 8.0 and 1 mM EDTA (hereinafter referred to as "TE buffer") were filtered through the membranes and the filtrate retained. Thereafter 20 mL TE buffer was directed through the membrane array, in order to wash non-bonded contamination out of the membranes. Then elution of the DNA was accomplished by directing 4 mL of a 2 M NaCl solution in TE buffer to obtain an eluate.

The filtrate and the eluate were sequentially diluted in a ratio of 1:10 with TE buffer, and tested by the LAL Test for the presence of endotoxins. With a UV spectro-photometer set at a wavelength of 260 nm (the absorption peak for DNA), the concentration of DNA in the filtrate and in the eluate was also determined. The yield of DNA was then set at 100%. In Table 1, the concentrations of DNA and endotoxin are shown, each reported concentration being the average of at least two trials.

TABLE 1

| Membrane | wt % DNA | | wt % Endotoxin | |
|---|---|---|---|---|
| | in filtrate | in eluate | in filtrate | in eluate |
| Sartobind ® D weakly basic | 3.5 | 50 | 2.0 | 1.6 |
| PP* | 10 | 1.2 | 0 | 0 |

TABLE 1-continued

| Membrane | wt % DNA | | wt % Endotoxin | |
|---|---|---|---|---|
| | in filtrate | in eluate | in filtrate | in eluate |
| Sartobind ® strongly basic | 3.3 | 33 | 17 | 16 |

*irreversible binding

Example 2

In a first trial three of the same weakly basic anion exchange membranes as in Example 1 were stacked in a stainless steel filter holder and first flushed with 20 mL water. Subsequently, 3 mL of the same feed solution of Example 1 were filtered through the membranes and the filtrate retained. Thereafter 20 ml TE buffer was directed through the membrane array, in order to wash out non-bonded contamination. Elution was accomplished as in Example 1.

In a second trial elution was conducted with a solution of 2 M NaCl in 10 mM sodium acetate buffer at pH 5.5. The filtrate and eluate were sequentially diluted in a ratio of 1:10 with TE buffer and tested for the presence of endotoxin and DNA as in Example 1; the reported concentrations represent the average of at least two trials.

TABLE 2

| Trial No. | wt % DNA | | wt % Endotoxin | |
|---|---|---|---|---|
| | in filtrate | in eluate | in filtrate | in eluate |
| 1 | 11 | 68 | 2.7 | 1.6 |
| 2 | 11 | 58 | 0.7 | .16 |

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A process for the purification of nucleic acids comprising the following steps:
    (a) directing an aqueous feed solution consisting essentially of a buffered solution containing at least one nucleic acid and at least one endotoxin through at least one microporous weakly basic anion exchange membrane so as to bind at least a portion of both said nucleic acid and said endotoxin to said membrane; and
    (b) directing an elution solution consisting essentially of a buffered neutral salt solution of 2M NaCl at pH 5.5 through said membrane so as to selectively elute from said membrane at least a major portion of said nucleic acid bound to said membrane in step (a)
    wherein the buffer used in steps (a) and (b) comprises an aqueous solution of tris-HCl and EDTA at pH 8.0 wherein the concentration ratio of tris-HCl to EDTA is 10 to 1.

2. The process of claim 1 further comprising passing said buffer through said at least one membrane between steps (a) and (b) so as to flush non-bonded and non-absorbed contamination from said membrane.

3. The process of claim 1 or 2 wherein said membrane contains a weakly basic anion exchange group selected from the group consisting of primary, secondary and tertiary amino groups.

* * * * *